US011389267B2

(12) United States Patent
DiCarlo et al.

(10) Patent No.: US 11,389,267 B2
(45) Date of Patent: **\*Jul. 19, 2022**

(54) WAVEBAND-SELECTIVE IMAGING SYSTEMS AND METHODS (71) Applicant: Intuitive Surgical Operations, Inc., Sunnyvale, CA (US)

(72) Inventors: Jeffrey M. DiCarlo, Austin, TX (US); Ian E. McDowall, Woodside, CA (US); Jonathan M. Sorger, Belmont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 16/775,806

(22) Filed: Jan. 29, 2020

(65) Prior Publication Data

US 2020/0179079 A1 Jun. 11, 2020

Related U.S. Application Data

(63) Continuation of application No. 15/536,210, filed as application No. PCT/US2015/065561 on Dec. 14, 2015, now Pat. No. 10,588,711.

(Continued)

(51) Int. Cl.
*A61B 90/00* (2016.01)
*A61B 34/30* (2016.01)
(Continued)

(52) U.S. Cl.
CPC .......... *A61B 90/37* (2016.02); *A61B 1/00011* (2013.01); *A61B 6/4057* (2013.01);
(Continued)

(58) Field of Classification Search
CPC ................. A61B 90/37; A61B 34/30
(Continued)

(56) References Cited

U.S. PATENT DOCUMENTS 5,408,996 A 4/1995 Salb
5,590,660 A 1/1997 Macaulay et al.
(Continued)

FOREIGN PATENT DOCUMENTS

JP H10500588 A 1/1998
JP 2003528684 A 9/2003
(Continued)

OTHER PUBLICATIONS

Extended European Search Report for Application No. EP20180104.0 dated Sep. 16, 2020, 5 pages.
(Continued)

*Primary Examiner* — Nadia A Mahmood (57) ABSTRACT

An exemplary surgical system is configured to 1) access a plurality of surgical site scenes captured entirely outside a structure within a patient, each surgical site scene in the plurality of surgical site scenes being captured from reflected light of a different waveband of a plurality of wavebands, each waveband of the plurality of wavebands being reflected by structure tissue of the structure and non-structure tissue outside the structure; 2) detect a difference between spectral reflectances of each of the surgical site scenes in the captured surgical site scenes, and 3) identify, based on the detected difference between the spectral reflectances of each of the surgical site scenes in the captured surgical site scenes, pixels in the captured surgical site scenes that correspond to the structure tissue and pixels in the captured surgical site scenes that correspond to the non-structure tissue outside the structure.

20 Claims, 4 Drawing Sheets

Related U.S. Application Data (60) Provisional application No. 62/092,651, filed on Dec. 16, 2014.

(51) Int. Cl.
*A61B 1/00* (2006.01)
*A61B 6/00* (2006.01)
*A61B 90/30* (2016.01)

(52) U.S. Cl.
CPC ........ *A61B 34/30* (2016.02); *A61B 2090/306* (2016.02); *A61B 2090/309* (2016.02); *A61B 2090/371* (2016.02); *A61B 2090/373* (2016.02)

(58) Field of Classification Search
USPC .......................................................... 600/431
See application file for complete search history.

(56) References Cited

U.S. PATENT DOCUMENTS

| | | |
|---|---|---|
| 10,588,711 B2 | 3/2020 | DiCarlo et al. |
| 2006/0004292 A1 | 1/2006 | Beylin |
| 2007/0027362 A1 | 2/2007 | Handa et al. |
| 2009/0156900 A1 | 6/2009 | Robertson |
| 2011/0059023 A1 | 3/2011 | Tunnell et al. |
| 2012/0316396 A1 | 12/2012 | Robertson |
| 2014/0005684 A1 | 1/2014 | Kim et al. |
| 2017/0360526 A1 | 12/2017 | Dicarlo et al. |

FOREIGN PATENT DOCUMENTS

| | | |
|---|---|---|
| JP | 2009226072 A | 10/2009 |
| JP | 2014128423 A | 7/2014 |
| WO | WO-2012098798 A1 | 7/2012 |
| WO | WO-2013177061 A1 | 11/2013 |

OTHER PUBLICATIONS

Extended European Search Report for Application No. EP15870805.7, dated Jun. 26, 2018, 7 pages.

Gaines K.K., "Phenazopyridine Hydrochloride: The Use and Abuse of an Old Standby for UTI," Urologic Nursing, Jun. 2004, vol. 24 (3), pp. 207-209.

International Preliminary Report on Patentability for Application No. PCT/US2015/065561, dated Jun. 29, 2017, 7 pages.

International Search Report and Written Opinion for Application No. PCT/US2015/065561, dated Mar. 2, 2016, 11 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

WAVEBAND-SELECTIVE IMAGING SYSTEMS AND METHODS

RELATED APPLICATIONS

This application is a continuation of U.S. patent application Ser. No. 15/536,210, filed Jun. 15, 2017, which application is the U.S. national phase of International Application No. PCT/US2015/065561, filed Dec. 14, 2015, which claims priority to U.S. Provisional Patent Application 62/092,651, filed Dec. 16, 2014, the contents of each of which are incorporated herein by reference.

BACKGROUND

Field of the Invention

The present invention relates generally to imaging techniques used in surgical procedures, and more particularly to ureter detection and imaging during surgical procedures.

Description of Related Art

A ureter is a narrow tube that carries urine from a kidney to the bladder. Muscles in the ureter walls continually tighten and relax forcing urine downward, away from the kidneys. About every ten to fifteen seconds, small amounts of urine are emptied into the bladder from the ureters.

Injury to ureters is an adverse event associated with surgery involving the pelvis or colorectal region. To prevent injury to the ureters during surgery, several different techniques have been tried to assist the surgeon in locating the ureters. For example, the surgeon can call an urologist to thread a small scope with a camera into the urethra to place a wire into each of the two ureters. Alternatively, lighted stents can be inserted through the urethra and up through the urinary bladder to access the ureters. However, both of these approaches are disruptive to the clinical workflow in a majority of benign surgical procedures and an urologist may not be available in some instances.

In another technique to determine the location of the ureters, a small amount of a radioactive chemical dye (TC99-DTPA) is injected through a vein in the patient's arm. The radioactive chemical dye passes through the body and is excreted through the urine, and so the radioactive chemical dye passes through the ureters. The ureters are detected by a hand held probe that senses the radioactivity.

In still another technique to locate the ureters, an IV injection, or a catheter-based retrograde injection of a near infrared (NIR) fluorophore is used to image the ureters using infrared illumination. It was reported that the ureters could be visualized even when embedded in surrounding tissue, and injury could be assessed in real time using invisible light. Eiichi Tanaka, et al. "Real-Time Intraoperative Ureteral Guidance Using Near-Infrared Fluorescence," *J. Urol.* 178(5), pgs. 2197-2201 (2007) describe using Indocyanine green (ICG) and CW800-CA, the carboxylic acid form of IRDye™ 800CW NIR dye, from LI-COR (Lincoln, Nebr.) as the NIR fluorophores. Aya Matsui, M. D., et al., "Real-Time Near-Infrared Fluorescence-Guided Identification of the Ureters using Methylene Blue," *Surgery*, 148(1) pgs. 78-86 (2010) use methylene blue as the NIR fluorophore.

Another approach to locate the ureters used infrared thermography. Room-temperature saline was used as an irrigant in the operative field so that the whole operative field was cooled temporarily. As the operative field differentially rewarmed, structures such as blood vessels rewarmed quickly and appeared as white lines against a dark background in an infrared image. A second application of this same concept involved filling the upper urinary system with room-temperature saline. The pelvis and ureter appeared black against a warmer background, which appeared white in an infrared image. See Jeffrey A. Cadeddu, M. D., et al, "Laparoscopic Infrared Imaging," *Journal of Endourology*, Vol. 15, No. 1, pgs. 111-116 (2001).

SUMMARY

Unlike the known techniques used to locate ureters that require introduction of a fluorophore, creation of a temperature difference, introduction of an object into the ureters, or introduction of a radioactive dye, selective reflection of light by ureters and by tissue around the ureters is used to safely and efficiently image the ureters. Thus, endogenous contrast is used to visualize ureters without need for illuminating catheters or the administration, for example, of exogenous fluorophores or radioactive dyes.

In one aspect, a plurality of surgical site scenes is captured. Each of the plurality of surgical site scenes is captured from reflected light having a different light spectrum. In one aspect the plurality of surgical site scenes is captured about simultaneously, i.e., within the timing and optical tolerances associated with capturing scenes at the same time, while in another aspect the plurality of surgical site scenes is captured sequentially.

The plurality of captured surgical site scenes is analyzed to identify ureter tissue in the captured surgical site scenes. A surgical site scene is displayed on a display device based on the captured surgical site scenes. The displayed surgical site scene has ureter tissue highlighted so that the ureter tissue is easily discerned by the surgeon.

In one aspect, a surgical site is illuminated with a plurality of different light spectrums. For example, the surgical site is illuminated sequentially with at least two of the plurality of different light spectrums. In one aspect, the plurality of light spectrums includes a light spectrum of wavelengths in a range from 450 nm to 580 nm, a light spectrum of wavelengths in a range from 640 nm to 750 nm, and a light spectrum of wavelengths in a range from 900 to 1080 nm.

In one aspect, the analysis of the plurality of captured surgical site scenes to identify ureter tissue first transforms a location in the surgical site scene in each of the plurality of captured surgical site scenes into a ureter signal. The analysis next determines whether the ureter signal is indicative of ureter tissue at the location. For example, the ureter signal is compared with a threshold. Alternatively, a ratio of the ureter signal and a non-ureter signal is compared with a threshold.

In yet another aspect, the ureter tissue is treated with a dye prior to the capturing of the surgical site scenes. The dye is different from a fluorophore and a radioactive dye, e.g., the dye is Phenzaopyridine.

To carry out these methods, a surgical system includes an image capture system. The image capture system is configured to capture a plurality of surgical site scenes. Each surgical site scene in the plurality of surgical site scenes is captured from reflected light of a different waveband in a plurality of wavebands. The surgical system also includes a ureter analysis module coupled to the image capture system. The ureter analysis module is configured to identify ureter tissue in the captured surgical site scenes. The surgical system, in one aspect, also includes an illuminator. The illuminator is configured to illuminate a surgical site with each of the plurality of wavebands. A display device of the surgical system is coupled to the ureter analysis module to receive a surgical site scene and information identifying the ureter tissue in that scene. The display device is configured to display the surgical site scene with a ureter highlighted.

BRIEF DESCRIPTION OF THE DRAWINGS

In the drawings, the first digit of a reference number indicates the figure in which the element with that reference number first appeared.

DETAILED DESCRIPTION

Unlike the known techniques used to locate ureters that require introduction of a fluorophore, creation of a temperature difference, introduction of an object into the ureters, or introduction of a radioactive dye, a ureter analysis module 135 locates the ureters using light reflected by the ureters. The selective reflection of light by the ureters and by the tissue around the ureters is used to safely and efficiently image the ureters. Thus, endogenous contrast is used to visualize ureters without need for illuminating catheters or the administration, for example, of exogenous fluorophores or radioactive dyes.

Figure 1:
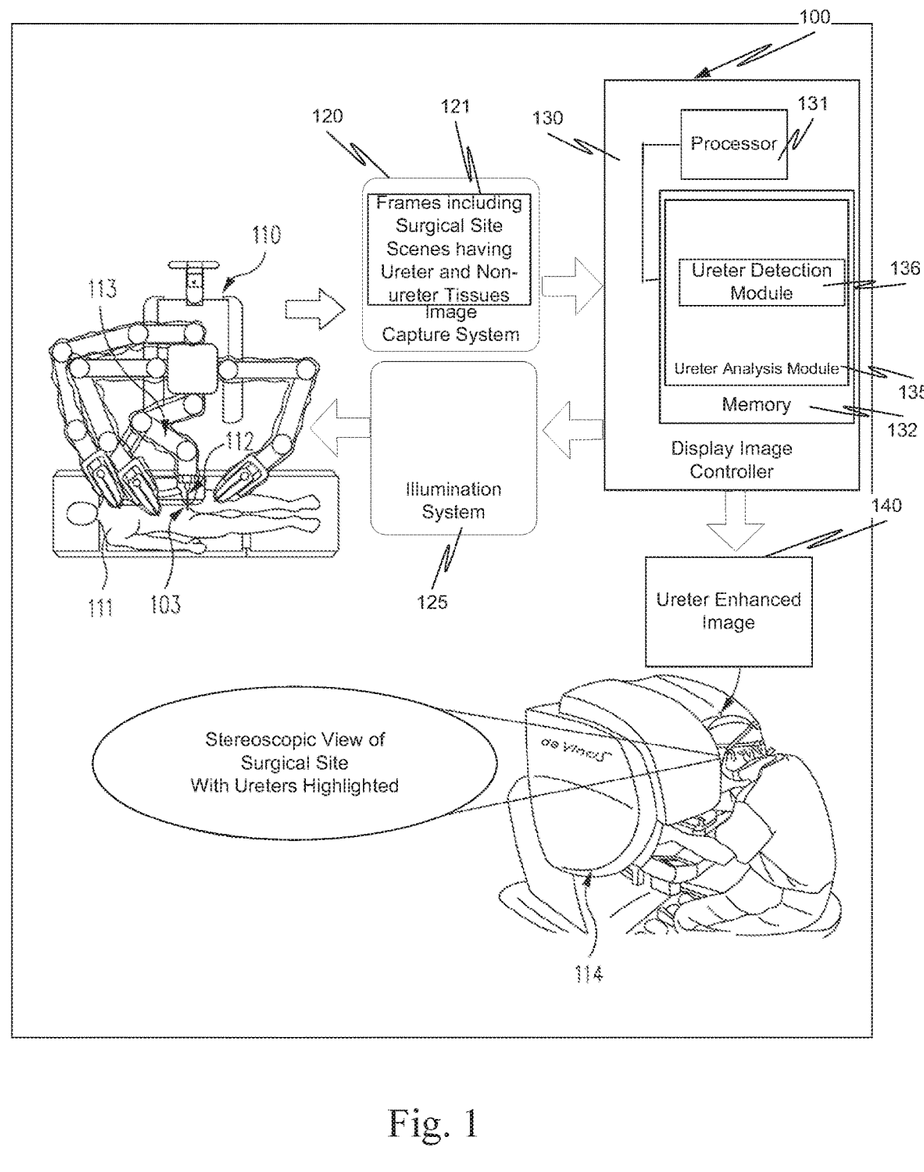
FIG. 1 is a high level diagram of a surgical system that includes a ureter analysis module.

FIG. 1 is a high-level diagrammatic view of a surgical system 100, for example, the da Vinci® Surgical System, including a ureter analysis module 135. (da Vinci® is a registered trademark of Intuitive Surgical, Inc. of Sunnyvale, Calif.) In this example, a surgeon, using master controls at a surgeon's console 114, remotely manipulates an endoscope 112 mounted on a robotic manipulator arm 113 that in turn is mounted on cart 110. The surgeon also remotely manipulates one or more surgical instruments coupled to cart 110. There are other parts, cables, etc. associated with the da Vinci® Surgical System, but these are not illustrated in FIG. 1 to avoid detracting from the disclosure.

Further information regarding minimally invasive surgical systems may be found for example in U.S. Pat. No. 9,060,678 (filed Jun. 23, 2007; disclosing Minimally Invasive Surgical System), U.S. Pat. No. 6,837,883 B2 (filed Oct. 5, 2001; disclosing Arm Cart for Telerobotic Surgical System), and U.S. Pat. No. 6,331,181 (filed Dec. 28, 2001; disclosing Surgical Robotic Tools, Data Architecture, and Use), all of which are incorporated herein by reference. The use of a teleoperated minimally invasive surgical system is illustrative only and is not intended to limit the invention to this specific system. In view of this disclosure, the aspects described herein can be incorporated in a robotic surgical system or other surgical system that includes the elements necessary to implement the aspects described herein.

Endoscope 112, in one aspect, is a stereoscopic endoscope, and so includes two optical channels that pass light from surgical site 103 within patient 111, e.g., reflected light and/or fluorescence, to an image capture system 120. Surgical site 103 includes ureters and the tissue commonly found around ureters.

The light reflected by tissue in surgical site 103 including light reflected by the ureter is captured as a surgical site scene. Each captured surgical site scene includes an image of ureter tissue and an image of non-ureter tissue. Each captured surgical site scene is contained in a frame of data 121. In one aspect, a plurality of frames is captured, one frame for each of a plurality of wavebands that illuminate surgical site 103.

For a stereoscopic endoscope, the surgical site scene includes two scenes, a left scene and a right scene. Two sets of data frames, a left set and right set, are captured by image capture system 120. The two sets are processed by a ureter detection module 136 of ureter analysis module 135 to create a left ureter enhanced image and a right ureter enhanced image that are sent to a stereoscopic display unit in surgeon's control console 114. The left ureter enhanced image and the right ureter enhanced image are included in ureter enhanced image 140.

The left ureter enhanced image and the right ureter enhanced image are presented on the stereoscopic display unit in surgeon's control console 114, sometimes referred to as surgeon's console 114 or simply console 114, to create a three-dimensional scene of surgical site 103 with the ureters highlighted. As noted above, the identification of the ureters is done utilizing the difference between the reflectance of tissue surrounding the ureters and the reflectance of the ureters. No special fluorophores, radioactive dyes, temperature differences, or objected inserted into the ureters are needed. Rather, ureter analysis module 135 is configured to use a difference between the spectral reflectance of ureters and the spectral reflectance of tissue surrounding the ureters (non-ureter tissue) to identify and display locations of the ureters in surgical site 103.

Figure 2:
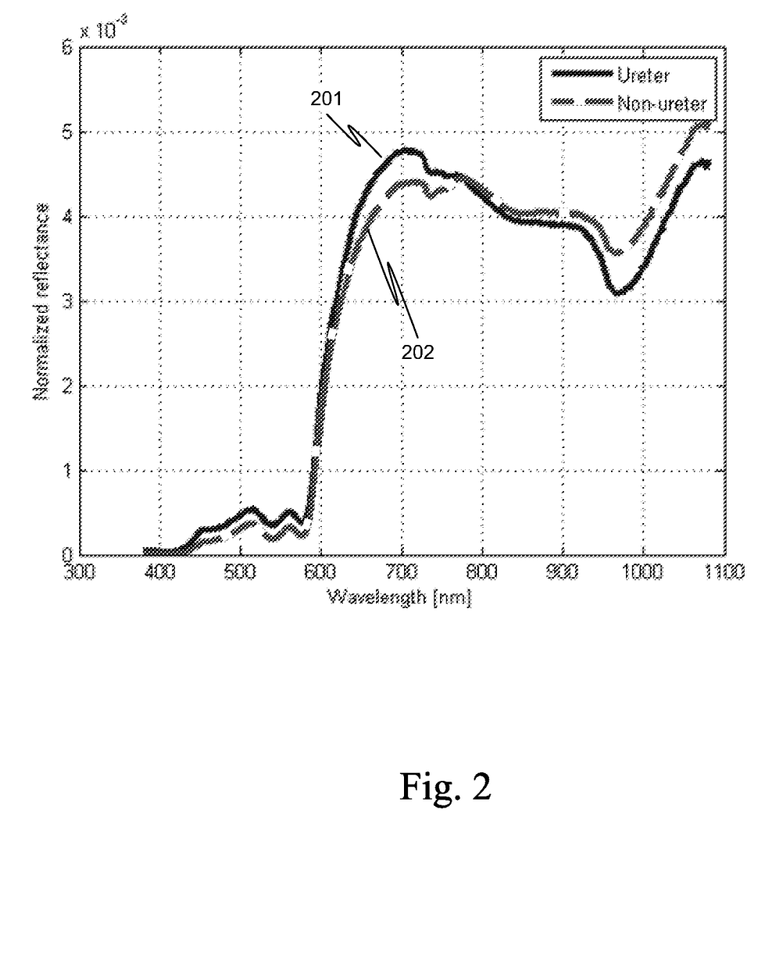
FIG. 2 is a graph that illustrates a plurality of light wavebands that are reflected differently by ureter tissue and non-ureter tissue.

FIG. 2 shows spectral reflectance 201 (solid line) of a ureter, i.e., a ureter spectral signature 201, as well as spectral reflectance 202 (dotted-line) of non-ureter tissue that is in close proximity to ureter tissue i.e., a non-ureter spectral signature 202. While visually it is very hard for a human to detect the color difference between ureter spectral signature 201 and non-ureter spectral signature 202, differences do exist as illustrated in FIG. 2.

Three separate wavebands, e.g., three separate light spectrums, have distinct reflectance differences between ureter tissue and non-ureter tissue. The three separate wavebands are 450 to 580 nanometers (nm) (a low waveband), 640 to 750 nm (a middle waveband), and 900 to 1080 nm (a high waveband). Sometimes, these wavebands are referred to as spectrums.

While the low waveband (450 to 580 nm) is in the visible light spectrum and the middle waveband (640 to 750 nm) is partially in the visible light spectrum (the visible light spectrum is taken as being between 400 nm and 700 nm), reflected visible light in these wavebands does not result in a color difference that is discernable by the surgeon in the scenes displayed on surgeon's console 114. The color difference associated with the reflectance differences is seen more as a slight intensity difference, and small intensity differences are difficult to detect by the human eye in complex lighting and three-dimensional scene structures, which are typical in surgical site scenes displayed on surgeon's console 114.

The other part (700 to 750 nm) of the middle waveband (640 to 750 nm) and the high waveband (900 to 1080 nm) are in the near infrared (NIR) portion of the electromagnetic spectrum. Near-infrared light is not detectable by a human. However, ureter detection module 136 detects the differences in spectral reflectance in all three of these wavebands and so can identify the pixels in a scene captured by image capture system 120 that correspond to ureter tissue and the pixels in that scene that correspond to non-ureter tissue.

In one aspect, the pixels in a scene that correspond to ureter tissue are highlighted, e.g., false-colored to have a color not typically seen in a surgical site scene, and the resulting scene is displayed on surgeon's console 114. The highlighted ureters allow the surgeon to easily discern the locations of the ureters during the surgical procedure.

In one aspect, ureter analysis module 135 configures illumination system 125 to illuminate the tissue including the ureters with at least two different light spectrums. The light spectrums selected are based on their differences in reflectance between ureter tissue and non-ureter tissue. Each spectrum is reflected differently by tissue surrounding the ureters and by the ureters as illustrated in FIG. 2. In another aspect, filters are used in image capture system 120 to capture frames corresponding to the different light spectrums having differences in reflectance between ureter tissue and non-ureter tissue.

The use of a stereoscopic endoscope and a stereoscopic display are illustrative only and are not intended to be limiting. The aspects described herein can be applied to systems that do not include the stereoscopic features such as monoscopic endoscopes and/or normal display units.

Figure 3:
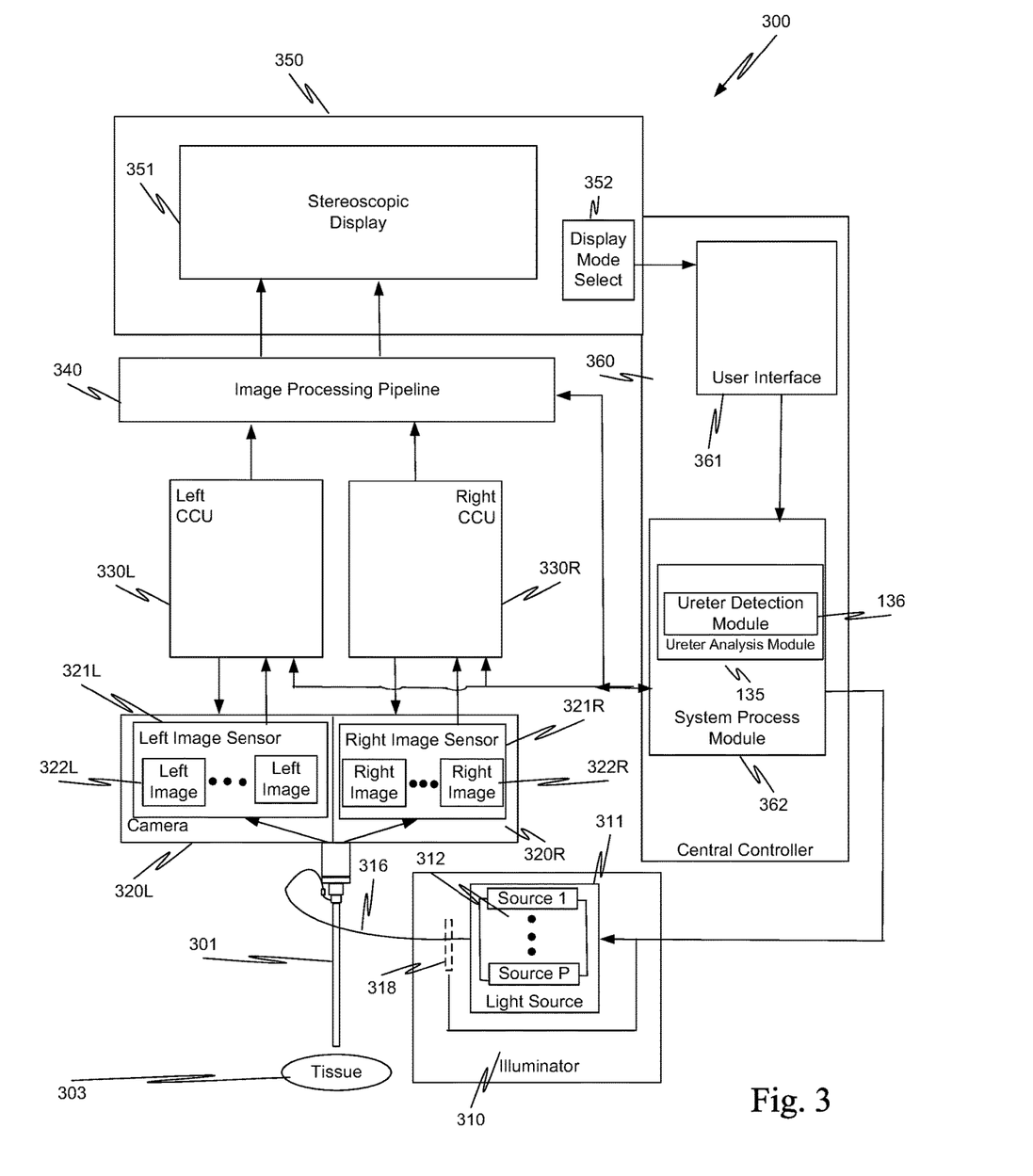
FIG. 3 is a more detailed block diagram of the parts of the surgical system of FIG. 1.

FIG. 3 is a more detailed illustration of aspects of one example of surgical system 100 of FIG. 1. In the embodiment of surgical system 300, an illuminator 310 is coupled to stereoscopic endoscope 301. Illuminator 310 includes at least a white light source and optionally may include one or more infrared illumination sources.

Illuminator 310 is used in conjunction with at least one illumination channel in stereoscopic endoscope 301 to illuminate surgical site 303. Alternatively and without loss of generality, illuminator 310 may be replaced by an illumination source at the distal tip, or near the distal tip, of endoscope 301. Such distal tip illumination may be provided by light emitting diodes (LEDs), for example, or other illumination sources.

In one example, illuminator 310 provides white light illumination that illuminates surgical site 303. In some implementations, illuminator 310 can also provide other types of illumination, e.g., non-visible light as well as a subset of the visible color components that make-up white light.

Light from illuminator 310 is directed onto an illumination channel 316 that couples illuminator 310 to the illumination channel in endoscope 301. The illumination channel in stereoscopic endoscope 301 directs the light to surgical site 303. The illumination channels can be implemented, for example, with a fiber optic bundle, a single stiff or flexible rod, or an optical fiber.

In one aspect, each of image capture units 320R, 320L includes an image capture sensor 321L, 321R that captures light reflected from surgical site 303. Each of image capture sensors 321L, 321R can be multiple CCDs that each capture a different visible color component; a single CCD with different regions of the CCD that capture a particular visible color component, etc.; a three-chip CCD senor; a single CMOS image sensor with a color filter array; or a three-CMOS color image sensor assembly, for example.

Irrespective of the implementation of each of image capture sensors 321L, 321R, Each of image capture units 320R, 320L and consequently each of image capture sensors 321R, 321L captures a plurality of frames of data 322L, 322R. In one aspect, the plurality of frames of data includes a frame for each of a plurality of wavebands that illuminate the surgical site. The frame of data that is captured for each waveband of the plurality of wavebands includes a surgical site scene that in turn includes ureter tissue and non-ureter tissue.

Image capture unit 320L is coupled to a stereoscopic display unit 351 in surgeon's console 350 via a left camera control unit (CCU) 330L. Image capture unit 320R is coupled to stereoscopic display unit 351 in surgeon's console 350 via a right camera control unit (CCU) 330R. Camera control units 330L, 330R receive signals from a system process module 362 that controls gains, controls capturing images, controls transferring frames to and from ureter detection module 136, etc. System process module 362 represents the various controllers including the vision system controllers in system 300. Camera control units 330L, 330R may be separate units, or may be combined in a single dual controller unit. Also, ureter detection module 136 can be implemented in camera control units 330L, 330R.

Display mode select switch 352 provides a signal to a user interface 361 that in turn passes the selected display mode to system process module 362. Various vision system controllers within system process module 362 configure illuminator 310 to produce the desired illumination, configure left and right camera control units 330L and 330R to acquire the desired data, and configure any other elements needed to process the acquired frames so that the surgeon is presented the requested images in stereoscopic display unit 351. While in this aspect, the scenes displayed on a surgeon's console are discussed, the scenes can also be displayed on other monitors located in the operating room or elsewhere.

As shown in FIG. 3, user interface 361, system process module 362, and ureter analysis module 135 are grouped as a central controller 360 for descriptive purposes. Central controller 360 also typically includes color correction modules that transform the color of the scenes to a new desired color balance as determined by system process module 362. Optional image processing module 340 receives signals from central controller 360 and processes scenes from the color correction modules prior to display on stereoscopic display unit 351 in surgeon's console 350. The color correction modules and optional image processing module 340 are equivalent to modules in known surgical systems and so are not considered in further detail.

Below processing associated with a single video stream in a single channel is described. However, this processing is applied to the video streams in both the right and left channels that are provided to stereoscopic display unit 351 in surgeon's console 350. Also, stereoscopic processing equivalent to the prior art stereoscopic processing is done with respect to the scenes processed and produced by ureter analysis module 135. Since the stereoscopic processing is known, it is not considered in further detail.

In normal operation, i.e., where a color image of a surgical site is presented on stereoscopic display unit 351, image capture sensor 321R captures a plurality of scenes, one for each color channel in surgical system 300. In another aspect for a ureter analysis mode, appropriate band pass filters are used in image capture sensor 321R so that a plurality of scenes is captured, one for each of the low, medium, and high wavebands described above. Each of the plurality of band pass filters passes one of the plurality of wavebands that are reflected differently be ureter tissue and non-ureter tissue. In this aspect of the ureter analysis mode, illuminator 310 includes at least a white light source and an infrared illumination source.

In another aspect of the ureter analysis mode, surgical site 303 is simultaneously illuminated by a plurality of illumination sources 312, where each of the plurality of illumination sources provides a different light spectrum. Each of the different light spectrums is reflected differently by ureter tissue and non-ureter tissue. In this aspect, the image capture sensor captures a scene for each different light spectrum, i.e., a plurality of scenes are captured about simultaneously, i.e., within the timing and optical path tolerances associated with the surgical system with respect to capturing images at the same time.

While in this example a plurality of illumination sources 312 are used, this is illustrative only and is not intended to be limiting. Alternatively, a plurality of filters 318 could be used to filter the light from light source 311 to provide each of the different wavebands of light to surgical site 303.

Each of the following configurations are equivalent with respect to providing frames for analyzing the location of ureter tissue: (1) a camera that has three color filters designed to pass the low, middle, and high wavebands and a broadband light that emits energy over all three wavebands, (2) a camera that has only one sensor that is sensitive to all three wavebands and three separate narrowband lights that emit energy in each of these three wavebands that are turned on sequentially and detected by the camera one at a time, and (3) some combination of (1) & (2).

Hence, irrespective of the technique used, in this example, three frames, i.e., a plurality of frames, are captured. One frame for each of the different wavebands that reflect differently from ureter tissue and non-ureter tissue is captured. Only one of the three captured frames could be analyzed to identify the ureter tissue in the frame. However, in some situations, specular reflections from non-ureter tissue or surgical instruments and/or depth variations in the tissue may make the single frame identification of ureter tissue problematic. Thus, in one aspect, at least two frames are used to identify the ureter tissue in the captured surgical site scenes.

Pixels at a same location in the captured surgical site scene in each of the frames or in a combination of frames are analyzed to determine whether the pixels at that location are indicative of ureter tissue. If the pixels at the same location in different frames are indicative of ureter tissue, the location in the surgical site scene is identified as being ureter tissue and otherwise is identified as being other than ureter tissue. When all the pixels in the captured frames are analyzed, the locations of ureter tissue in the surgical site scene are known.

In one aspect, the scenes captured in the three frames are combined and displayed as a grey scale image, and the locations of ureter tissue are false colored, e.g., given a green color, and superimposed with the grey scale image for display on stereoscopic display 351.

Irrespective of how the plurality of frames of light reflected from each of the plurality of wavebands is obtained, it is necessary to transform the information in the plurality of frames into a ureter signal and a non-ureter signal at each location in the frames, in one aspect. In the following description, a location in each of the plurality of captured frames is analyzed to determine whether the pixels at that location in the plurality of frames represent a ureter signal or a non-ureter signal. This is for purposes of illustration only and is not intended to be limiting. In practice, a group of locations in a frame or even the entire frame would be processed in one transformation and the ureter signal or non-ureter signal determination made for each location in the group or frame.

Also, the locations being referred to are locations in the surgical site scene as opposed to absolute locations in the captured frames. For example, location (x, y) in the surgical site scene may be at location (x, y) in the captured frames for the first and second wavebands and at location (x+1, y−1) in the captured frame for the third waveband. This depends on whether the frames captured for the three wavebands are automatically spatially registered to each other. If the three frames are captured so that the frames are spatially registered to each other, the relationship between locations in the three different frames is fixed and known. An example of an image capture unit in which the captured frames are spatially registered to each other is presented in U.S. Pat. No. 8,672,838 B2 (issued Mar. 18, 2014, disclosing "Image Capture Unit in A Surgical Instrument"), which is incorporated herein by reference.

If the frames are not captured so that the frames are spatially registered to each other, the three captured frames are spatially registered to one another so that the same location in the surgical site scene is processed from each of the frames. Spatial registration is known and so is not considered if further detail. See for example, Maintz and Viergever, "An Overview of Medical Image Registration Methods," *In Symposium of Medical Image Registration Methods*, (1996), which is incorporated herein by reference. See also, Sotiras et al., "Deformable Medical Image Registration: A Survey," *IEEE Trans Med Imaging*, 32(7), pp. 1153-1190, (July 2013), which is incorporated herein by reference.

In one aspect of ureter detection module 136, a waveband to ureter signal transform C is applied to the waveband signals B to obtain ureter-based signals D at each location in the surgical site scene. For example, $$D = C * B$$

$$\begin{bmatrix} \text{ureter} \\ \text{non-ureter} \end{bmatrix} = \begin{bmatrix} UB1 & UB2 & UB3 \\ NB1 & NB2 & NB3 \end{bmatrix} * \begin{bmatrix} \text{Band1} \\ \text{Band2} \\ \text{Band3} \end{bmatrix}$$

where
Band1, Band2, and Band3 are waveband signals representing the captured surgical site scenes for the low, middle, and high wavebands, respectively;
UB1, UB2, UB3 are a first plurality of weights that convert plurality of waveband signals Band1, Band2, and Band3 to a ureter signal ureter; and
NB1, NB2, NB3 are a second plurality of weights that convert plurality of waveband signals Band1, Band2, and Band3 to a non-ureter signal non-ureter.

After waveband signals Band1, Band2, and Band3 are transformed to a ureter signal ureter and to a non-ureter signal non-ureter, the ureter and non-ureter signals are analyzed to determine if it is more likely that the camera is looking at ureter tissue or non-ureter tissue at each location.

In one aspect, thresholding is performed to determine whether the camera is looking at ureter tissue or non-ureter tissue. For example, an empirical threshold is determined such that when ureter signal ureter has a predetermined relationship to the threshold, ureter signal ureter is taken as being from ureter tissue. The empirical threshold is determined, for example, by illuminating ureter tissue from several different sources, capturing images of the ureter tissue as described above, and performing the transformation just described to determine ureter signal ureter for each of the different ureter sources. In one aspect, the smallest ureter signal ureter$_{small}$ is taken as the threshold.

In another aspect, the thresholding divides ureter signal ureter by non-ureter signal non-ureter at each location in the frame, i.e., forms a ratio of the two signals, and compares the ratio with an empirical threshold, e.g., determines whether ureter signal ureter is some constant or multiple greater than non-ureter signal non-ureter. Again, the threshold is determined by using several samples containing ureter tissue and non-ureter tissue in the process described above to obtain ureter signal ureter and non-ureter signal non-ureter for the samples. These signals are used to determine the threshold.

Thresholding removes noise and false positives from ureter signal ureter. Due to noise, ureter signal ureter is quite frequently slightly above zero even though the ureter is not present. Using a threshold allows removing this noise to remove the false positives. Thresholding also allows determining the confidence about the ureter detection before displaying a location in the frame as representing ureter tissue to the surgeon. If a high level of confidence is desired, a high threshold is used. If displaying false positives is acceptable, the threshold is set lower. The magnitude of the threshold determines the level of ureter signal ureter required to label a location in the frame as being ureter tissue, and so the threshold really is the level of confidence the system has that the ureter is actually at that location in the frame.

Figure 4:
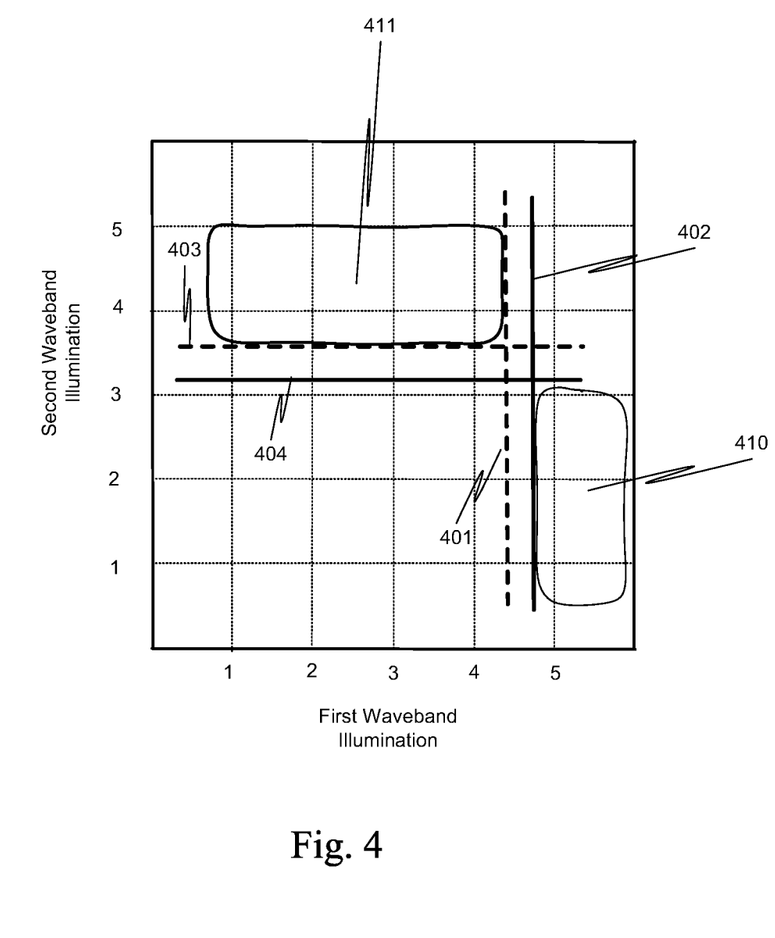
FIG. 4 is a graph showing one way to differentiate between ureter and non-ureter signals.

In still another aspect, ureter signal ureter vs. non-ureter signal non-ureter is mapped onto a two-dimensional space, and the region of this space that it is highly probably the camera is looking at ureter tissue is detected. FIG. 4 is an example of how the two-dimensional space is determined for two wavebands. In FIG. 4, the middle waveband signals are plotted along the x-axis and the high waveband signals are plotted along the y-axis. For purposes of an example only, the middle waveband is taken as having a wavelength of 700 nm, and the high waveband is taken as having a wavelength of about 960 nm. Using FIG. 2 for the middle waveband, non-ureter signal non-ureter is scattered about dashed vertical line 401, and ureter signal ureter is scattered about solid vertical line 402. For the high waveband, non-ureter signal non-ureter is scattered about dashed horizontal line 403, and ureter signal ureter is scattered about solid horizontal line 404.

Thus, signals that fall within region 411 are non-ureter signals non-ureter, and signals that fall within region 410 are ureter signals ureter. In practice, images of a number of different ureter samples are captured using the two actual wavebands, and the non-ureter signals non-ureter and the ureter signals ureter obtained using the transformation described above are plotted. Regions 410 and 411 are defined, and lines determined that bound the region of ureter signals ureter. Then in a clinical setting, if a ureter signals ureter at a given location falls within region 410, the location is marked as having ureter tissue, and otherwise the location is considered to have non-ureter tissue.

After a frame is processed and a determination is made that a region in the camera's view is the ureter, the frame is displayed to the surgeon with that region being differentiated from the remainder of the scene. There are again multiple ways to display this information so that the ureter is differentiated from the rest of the surgical site scene. One way is to include a color overlay over the ureter tissue to alert the surgeon that the ureter is there. Another way is to change the color of the ureter tissue significantly in the displays—the false coloring described above—so that the surgeon sees the ureter tissue as being different from the surrounding tissue. While yet another way is to display warning signs on top of the ureter tissue to signal to the surgeon the presence of the ureter. In all of these cases, such on overlay or color changes, in one aspect, can be controlled by the surgeon, i.e., the surgeon can turn on or off the highlighting of the ureters or increase or decrease the color shifts that are applied to visualize the ureters.

In some aspect, transform C, as described above, is not used, and the thresholding is applied directly in a waveband space using the waveband signals to determine whether the location is ureter tissue. In another aspect, the ureter signal that comes from applying transform C is used directly to display the presence or absence of the ureter.

First plurality of weights UB1, UB2, UB3 and second plurality of weights NB1, NB2, NB3 in waveband to ureter signal transform C can be determined multiple ways. For example, the first and second pluralities of weights can be determined by first empirically measuring the waveband signals directly reflected by ureter and non-ureter tissue; by modeling the camera/lighting system and the reflectance of ureter and non-ureter tissue; or by some combination of empirical measurement and modeling. Each of these approaches produces a set of waveband signals that correlate to ureter tissue and a set of waveband signals that correlate to non-ureter tissue.

The first and second pluralities of weights are determined combining the set of waveband signals that correlate to ureter tissue and the set of waveband signals that correlate to non-ureter tissue and solving for the matrix that minimizes the error. For example, $$DU: \begin{bmatrix} 1 & 1 & ... & 1 \\ 0 & 0 & ... & 0 \end{bmatrix} \quad BU: \begin{bmatrix} U11 & U12 & ... & U1N \\ U21 & U22 & ... & U2N \\ U31 & U32 & ... & U3N \end{bmatrix}$$

$$DN: \begin{bmatrix} 1 & 1 & ... & 1 \\ 0 & 0 & ... & 0 \end{bmatrix} \quad BN: \begin{bmatrix} N11 & N12 & ... & U1M \\ N21 & N22 & ... & U2M \\ N31 & N32 & ... & U3M \end{bmatrix}$$

$$C = [DU\ DN] * pinv([BU\ BN])$$

where
  DU is a matrix to select the ureter signals;
  BU is a matrix of the frames captured for each of the three wavebands for N ureter samples:
  DN is a matrix to select the non-ureter signals;
  BN is a matrix of the frames captured for each of the three wavebands for M non-ureter samples; and
  pin v is a pseudo inverse.

A pseudo inverse of a matrix is known to those knowledgeable in the field. A pseudo inverse suitable to use here is referred to as the Moore-Penrose pseudo inverse. A common use of the Moore-Penrose pseudo inverse is to compute a 'best fit' least squares solution to the system of linear equations, which lacks a unique solution. Another use of the Moore-Penrose pseudo inverse is to find the minimum (Euclidean) norm solution to the system of linear equations. In one aspect, the best fit least squares solution is used.

In the above example, a plurality of different light spectrums illuminated a surgical site and a frame including a surgical site scene was captured for each of the different light spectrums, which resulted in a plurality of frames being captured. The plurality of frames was analyzed to classify locations in the surgical site scene that were ureter tissue. In another aspect, this same method is used, but the patient has taken a dye prior to the surgery. The dye is different from both a fluorophore and a radioactive dye. A fluorophore absorbs light having an excitation wavelength spectrum and emits light having an emission wavelength spectrum. The process is absorption of incident light by the fluorophore and emission of new light by the fluorophore as contrasted with reflection of the incident light. A radioactive dye gives off radiation that is measured without requiring any incident light. The dyes used in this aspect do not emit either new light or radiation, but instead the dyes affect the reflection of the incident light.

One example of such a dye is Phenazopyridine, sometimes used in the form of Phenazopyridine Hydochloride. Phenazopyridine is a dye that works as a urinary tract analgesic agent. Phenazopyridine is typically administered to a patient orally and is rapidly excreted by the kidneys directly into the urine. Hence, both the urine and the walls of the ureters are dyed by Phenazopyridine, which changes the light absorption properties of the ureters, and hence changes at least some of the light reflected by the ureters. Thus, in one aspect, Phenazopyridine is administered and the wavebands reflected by ureters tissue treated with Phenazopyridine are determined. These wavebands are used in the above analysis.

The various modules described herein can be implemented by software executing on a processor 131, hardware, firmware, or any combination of the three. When the modules are implemented as software executing on a processor, the software is stored in a memory 132 as computer readable instructions and the computer readable instructions are executed on processor 131. All or part of the memory can be in a different physical location than a processor so long as the processor can be coupled to the memory. Memory refers to a volatile memory, a non-volatile memory, or any combination of the two.

Also, the functions of the various modules, as described herein, may be performed by one unit, or divided up among different components, each of which may be implemented in turn by any combination of hardware, software that is executed on a processor, and firmware. When divided up among different components, the components may be centralized in one location or distributed across system 300 for distributed processing purposes. The execution of the various modules results in methods that perform the processes described above for the various modules and controller 360.

Thus, a processor is coupled to a memory containing instructions executed by the processor. This could be accomplished within a computer system, or alternatively via a connection to another computer via modems and analog lines, or digital interfaces and a digital carrier line.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives and other physical storage mediums.

In view of this disclosure, instructions used in any part of or all of the processes described herein can be implemented in a wide variety of computer system configurations using an operating system and computer programming language of interest to the user.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures.

For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

Likewise, descriptions of movement along and around various axes include various special device positions and orientations. The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

Components described as coupled may be electrically or mechanically directly coupled, or they may be indirectly coupled via one or more intermediate components. In view of this disclosure, instructions used in any one of, or any combination of operations described with respect to the augmented display system can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

What is claimed is:

1. A surgical system comprising:
a memory storing instructions; and a processor configured to execute the instructions to
  access a plurality of surgical site scenes captured entirely outside a structure within a patient, each surgical site scene in the plurality of surgical site scenes being captured from reflected light of a different waveband of a plurality of wavebands, each waveband of the plurality of wavebands being reflected by structure tissue of the structure and non-structure tissue outside the structure;
  detect a difference between spectral reflectances of each of the surgical site scenes in the captured surgical site scenes, and
  identify, based on the detected difference between the spectral reflectances of each of the surgical site scenes in the captured surgical site scenes, pixels in the captured surgical site scenes that correspond to the structure tissue and pixels in the captured surgical site scenes that correspond to the non-structure tissue outside the structure.

2. The surgical system of claim 1, wherein the processor is further configured to execute the instructions to:
  direct a display device to display a surgical site scene included in the plurality of surgical site scenes; and
  artificially highlight the pixels that correspond to the structure tissue in the displayed surgical site scene.

3. The surgical system of claim 1, wherein the processor is further configured to execute the instructions to direct an illuminator to illuminate a surgical site with a plurality of different light spectrums.

4. The surgical system of claim 3, wherein the directing the illuminator to illuminate the surgical site comprises directing the illuminator to illuminate the surgical site sequentially with at least two of the plurality of different light spectrums.

5. The surgical system of claim 3, wherein the directing the illuminator to illuminate the surgical site comprises directing the illuminator to:
  illuminate the surgical site with a first light spectrum of wavelengths in a range from 450 nm to 580 nm;
  illuminate the surgical site with a second light spectrum of wavelengths in a range from 640 nm to 750 nm; and
  illuminate the surgical site with a third light spectrum of wavelengths in a range from 900 to 1080 nm.

6. The surgical system of claim 3, wherein the directing the illuminator to illuminate the surgical site comprises directing the illuminator to:
  illuminate the surgical site with a first light spectrum of wavelengths in a range from 450 nm to 580 nm; and
  illuminate the surgical site with a second light spectrum of wavelengths illuminating the surgical site with a light spectrum of wavelengths in a range from 640 nm to 750 nm.

7. The surgical system of claim 1, wherein the identifying comprises:
  transforming a location in each of the plurality of captured surgical site scenes into a structure signal; and
  determining whether the structure signal is indicative of structure tissue at the location.

8. The surgical system of claim 7, wherein the determining comprises comparing the structure signal with a threshold.

9. The surgical system of claim 7, wherein the determining comprises comparing a ratio of the structure signal and a non-structure signal with a threshold.

10. The surgical system of claim 1, wherein the identifying comprises comparing a structure signal with a threshold.

11. The surgical system of claim 1, wherein the identifying comprises comparing a ratio of a structure signal and a non-structure signal with a threshold.

12. The surgical system of claim 1, wherein the structure tissue is treated with a dye, the dye being different from a fluorophore and a radioactive dye.

13. The surgical system of claim 12, the dye being Phenazopyridine.

14. The surgical system of claim 1, wherein:
  the structure is a ureter;
  the structure tissue is ureter tissue of the ureter; and
  the non-structure tissue is non-ureter tissue outside the ureter.

15. The surgical system of claim 1, wherein the plurality of surgical site scenes are captured with an endoscope located entirely outside the structure.

16. A method comprising:
  accessing a plurality of surgical site scenes captured entirely outside a structure within a patient, each surgical site scene in the plurality of surgical site scenes being captured from reflected light of a different waveband of a plurality of wavebands, each waveband of the plurality of wavebands being reflected by structure tissue of the structure and non-structure tissue outside the structure;
  detecting a difference between spectral reflectances of each of the surgical site scenes in the captured surgical site scenes;
  identifying, based on the detected difference between the spectral reflectances of each of the surgical site scenes in the captured surgical site scenes, pixels in the captured surgical site scenes that correspond to the structure tissue and pixels in the captured surgical site scenes that correspond to the non-structure tissue outside the structure.

17. The method of claim 16, further comprising:
  displaying a surgical site scene included in the plurality of surgical site scenes on a display device; and
  artificially highlighting the pixels that correspond to the structure tissue in the displayed surgical site scene.

18. The method of claim 16, wherein the identifying comprises:
  transforming a location in each of the plurality of captured surgical site scenes into a structure signal; and
  determining whether the structure signal is indicative of structure tissue at the location.

19. The method of claim 16, wherein:
  the structure is a ureter;
  the structure tissue is ureter tissue of the ureter; and
  the non-structure tissue is non-ureter tissue outside the ureter.

20. The method of claim 16, wherein the plurality of surgical site scenes are captured with an endoscope located entirely outside the structure.

* * * * *